United States Patent [19]

Fleet et al.

[11] Patent Number: 5,021,562

[45] Date of Patent: Jun. 4, 1991

[54] METHOD FOR AZIDE DISPLACEMENT OF α-TRIFLATES OF 1,5-LACTONES

[75] Inventors: George W. J. Fleet; Ian Bruce, both of Oxford, United Kingdom

[73] Assignee: Monsanto Company, St. Louis, Mo.

[21] Appl. No.: 524,514

[22] Filed: May 17, 1990

Related U.S. Application Data

[63] Continuation-in-part of Ser. No. 352,068, May 15, 1989, abandoned, and a continuation-in-part of Ser. No. 419,806, Nov. 11, 1989.

[51] Int. Cl.$^5$ .................. C07H 13/02; C07D 311/02
[52] U.S. Cl. ................................. 536/53; 536/119; 549/283; 549/285
[58] Field of Search .................. 549/283, 285; 536/53, 536/119

[56] References Cited

PUBLICATIONS

Fleet, Tetrahedron 45, 319–326, (1989).
Bashyal et al., Tetrahedron 43, 415–422 (1987).
Bashyal et al., Tetrahedron 43, 423–430 (1987).
Montgomery and Hudson, J. Am. Chem. Soc. 64, 247 (1942).
Karabinos et al., J. Am. Chem. Soc. 75, 4320 (1953).
Baird et al., J. Chem. Soc. Perkin Trans. 1, 1785–1791 (1987).
Dho et al., Tetrahedron Lett. 27, 3203–3204 (1986).
Nash et al., Tetrahedron 44, 5959–5964 (1988).
Kite et al., Tetrahedron Lett. 29, 6483–6486 (1988).
Fleet et al., Ibid. 25, 4029–4032 (1984).
Fleet et al., Tetrahedron 43, 979–990 (1987).

*Primary Examiner*—Mary C. Lee
*Assistant Examiner*—Joseph K. McKane
*Attorney, Agent, or Firm*—Scott J. Meyer; James W. Williams, Jr.

[57] ABSTRACT

Reactions of azide ion with 2-O-trifluoromethanesulphonates of both 3,4:6,7-di-O-isopropylidene-D-glycero-D-talo-heltono-1,5-lactone and of 3,4:6,7-di-O-isopropylidene-D-glycero-D-galactoheptono-1,5-lactone are disclosed to give predominantly 2-azido-2-deoxy-3,4:6,7-di-O-isopropylidene-D-glycero-D-galacto-heptono-1, 5-lactone initially which then isomerizes under moderate reaction conditions to 2-azido-2-deoxy-3,4:6,7-di-O-isopropylidene-D-glycero-D-talo-heptono-1, 5-lactone.

3 Claims, No Drawings

METHOD FOR AZIDE DISPLACEMENT OF α-TRIFLATES OF 1,5-LACTONES

CROSS-REFERENCE TO RELATED APPLICATIONS

This is a continuation-in-part of copending U.S. application Ser. No. 07/352,068, filed May 15, 1989, now abandoned and copending U.S. application Ser. No. 07/419,806, filed Nov. 11, 1989.

BACKGROUND OF THE INVENTION

The present invention relates to a method for azide displacement of α-triflates of 1,5-lactones.

Sugar lactones have been used heretofore as intermediates for the synthesis of highly functionalized nitrogen heterocycles. See Fleet et al., Tetrahedron, 45, 319–326 (1989) and references cited therein. See also U.S. Pat. No. 4,861,892 concerning the synthesis of deoxymannojirimycin from gulonolactone. The readily available acetonide of glucuronolactone, in which only the C-5 hydroxyl group α- to the carbonyl group is unprotected, has been used in the synthesis of a number of D- and L-amino acids. See Bashyal et al., Tetrahedron, 43, 415–422 (1987) and Bashyal et al., Ibid. 43, 423–430 (1987).

Suitably protected heptonolactones with seven adjacent functional groups and five adjacent chiral centres can provide powerful intermediates for the synthesis of complex and highly functionalized targets. The epimeric lactones (1) and (3) disclosed herein can be obtained as a mixture in which the lactone (1) predominates from the treatment of diacetone mannose (7) with sodium cyanide. The stereoselectivity in this reaction is in marked contrast to that observed in the reaction of cyanide with mannose. See Montgomery and Hudson, J. Am. Chem. Soc. 64, 247 (1942); Karabinos et al., Ibid. 75, 4320 (1953).

BRIEF DESCRIPTION OF THE INVENTION

In accordance with the present invention nucleophilic azide ion displacement of both the protected heptonolactone 2-O-trifluoromethanesulphonates (2) and (4), derived from (1) and (3), respectively, is carried out to predominantly give initially the azide (6) which is subsequently epimerized to azide (5) under moderate reaction conditions. Thus, the reaction of the triflates with azide cation, preferably alkali metal azide, e.g., sodium azide, can be carried out at normal room temperature (ca. 20°–25° C.) in organic solvent medium, e.g., dimethyl formamide, to yield the galacto-azide which is then epimerized to the talo-azide under these reaction conditions or by further addition of alkali metal acetate, e.g. sodium acetate.

In particular, the reactions of azide ion with 2-O-trifluoromethanesulphonates of both 3,4:6,7-di-O-isopropylidene-D-glycero-D-taloheptono-1,5-lactone and of 3,4:6,7-di-isopropylidene--glycero-D-galacto-heptono-1,5-lactone give predominantly 2-azido-2-deoxy-3,4:6,7-di-O-isopropylidene-D-glycero-D-galacto-heptono-1,5-lactone (6) initially which then isomerizes under the reaction conditions to 2-azido-2-deoxy-3,4:6,7-di-O-isopropylidene-D-glycero-D-talo-heptono-1,5-lactone (5). The latter talo-azide, with 5 adjacent chiral centers, is a novel intermediate which can be used for the synthesis of α-amino acids with seven adjacent functional groups and five adjacent chiral centers.

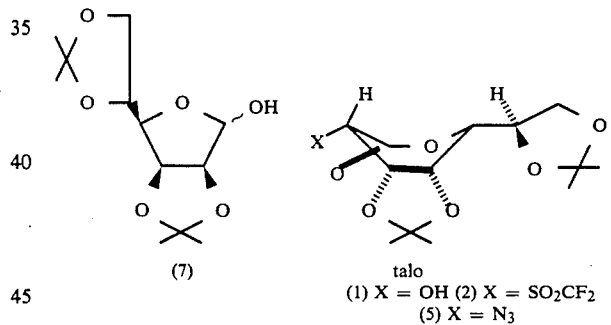

(7)

talo
(1) X = OH (2) X = SO₂CF₂
(5) X = N₃

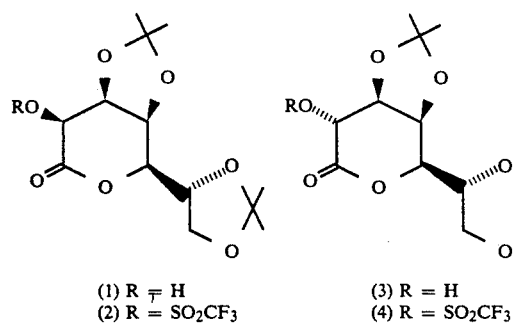

(1) R = H
(2) R = SO₂CF₃

(3) R = H
(4) R = SO₂CF₃

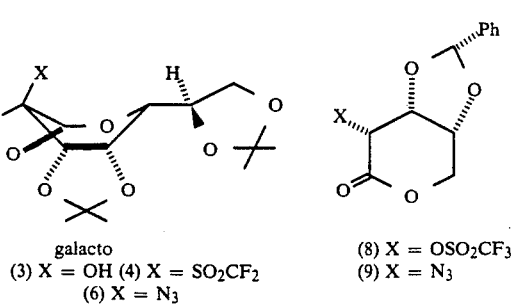

galacto
(3) X = OH (4) X = SO₂CF₂
(6) X = N₃

(8) X = OSO₂CF₃
(9) X = N₃

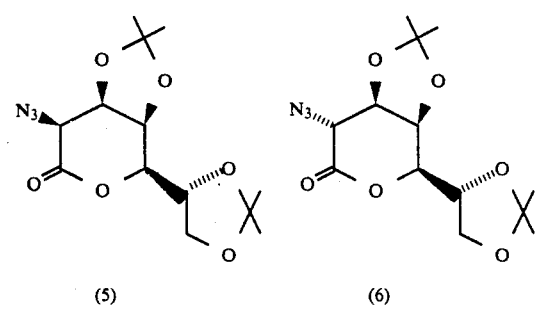

(5)

(6)

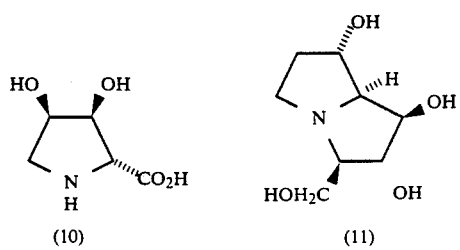

(10)

(11)

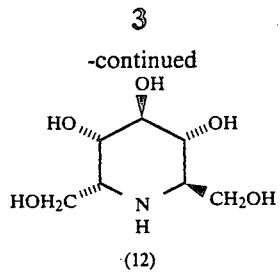

(12)

The novel 2-azido-2-deoxy-3,4:6,7-di-O-isopropylidene-D-glycero-D-galacto-heptono-1,5-lactone (5) also is useful for the synthesis of α-homomannojirimycin and 6-epi-homomannojirimycin, in which nitrogen is introduced at C-2. The respective systematic names for α-homomannojirimycin and 6-epi-homomannojirimycin are 2,6-dideoxy-2,6-iminoD-glycero-D-talo-heptitol and 2,6-dideoxy-2,6-imino-L-glycero-D-talo-heptitol.

In accordance with the latter synthesis the side chain acetonide in the azidolactone (5) is acid hydrolyzed to give the corresponding diol (13) which is then reacted with a silyl protecting agent, e.g. t-butyldimethylsilyl chloride, to give the silyl ether, 2-azido-7-O-tert-butyldimethylsilyl-2-deoxy-3,4-isopropylidene-D-glycero-D-talo-heptono1,5-lactone (14). The silyl ether (14) is then used as a divergent intermediate as follows:

A. to produce 6-epi-homomannojirimycin (6-epi-HMJ) by a synthetic method which comprises formation of the piperidine ring by joining the nitrogen function at C-2 to C-6 with inversion of configuration at C-6, or B. to produce α-homomannojirimycin (α-HMJ) by a synthetic method which comprises formation of the piperidene ring by joining the nitrogen function at C-2 to C-6 with retention of configuration at C-6.

See Examples 8 to 19, below, which illustrate the foregoing synthesis of 6-epi-HMJ and α-HMJ. α-HMJ and 6-epi-HMJ are useful glycosidase inhibitors as can be seen from the following tests.

GLYCOSIDASE INHIBITION TESTS.

The two iminoheptitols (α-HMJ) and (6-epi-HMJ) were assayed as inhibitors of 14 human liver glycosidases and the effects compared with those of deoxymannojirimycin by conventional enzyme assay methods described by Daher et al., Biochem. J. 258, 13 (1989). The results are set forth in the Table, below, in which it can be seen that the specificity and potency of inhibition of human α-mannosidas by α-HMJ and by DMJ is very similar. Neither compound inhibited β-mannosidase. 6-epi-HMJ did not inhibit any α-mannosidase, indicating that the correct configuration at C-5 is essential for the inhibition of α-mannosidases. In contrast, both DMJ and 6-epi-HMJ were powerful inhibitors of α-fucosidase, whereas α-HMJ is only a weak inhibitor of this enzyme. The relative potencies of these compounds as fucosidase inhibitors may be understood by considering them as analogues of α-L-fucose; all three compounds have the correct chirality of the secondary hydroxyl groups - the minimum requirement for inhibition of α-fucosidase. However, their relative effectiveness as α-fucosidase inhibitors is determined by the stereochemistry of the substituents at C-2 and C-6; while DMJ and 6-epi-HMJ have only one substituent with the wrong configuration relative to α-L-fucose, both substituents at C-2 and C-6 of α-HMJ are different from those in α-L-fucose. All the compounds are weaker inhibitors of α-fucosidase than is deoxyfuconojirimycin, since they all lack a lipophilic methyl substituent with correct configuration.

Thus α-HMJ is a more selective inhibitor of α-mannosidases than DMJ. The enhanced specificity of α-HMJ, relative to DMJ and the possibility of the formations of α-1,2,-, α-1,2- and α-1,2-mannosyl derivatives attached to the anomeric hydroxymethyl group should make this a valuable compound for exploring the function and specificity of the processing mannosidases. In summary, the present invention demonstrates the use of the novel talo-azide intermediate (5) in the synthesis of highly functionalized compounds and further indicates the potential of iminoheptitols as glycosidase inhibitors.

TABLE

% Inhibition of human liver α-fucosidase and α-mannosidase catalysed hydrolysis of 4-umbelliferyl pyrranosides at 1 mM concentration of inhibitor

| Inhibitor | α-Mannosidases | | | α-Fucosidase |
|---|---|---|---|---|
| | Lysosomal | Golgi II | Neutral | |
| Deoxymanno-jirimycin | 58% | 45% | 21% | 91% [$K_i$ 5.0 μM] |
| Homomanno-jirimycin | 49% | 56% | 30% | 29% |
| 6-Epi-homo-mannojiri-mycin | 0% | 0% | 0% | 96% [$K_i$ 4.5 μM] |

DETAILED DESCRIPTION OF THE INVENTION

The invention is conveniently illustrated by the following description of preferred embodiments in which the reactions of azide ion with 2-O-trifluoromethanesulphonates of both 3,4:6,7-di-O-isopropylidene-D-glycero-D-talo-heptono-1,5-lactone and of 3,4:6,7-di-O-isopropylidene-D-glycero-D-galacto-heptono-1,5-lactone give predominantly 2-azido-2-deoxy-3,4:6,7-di-O-isopropylidene-D-glycero-D-galacto-heptono-1,5-lactone initially which then isomerizes under the reaction conditions to 2-azido-2-deoxy-3,4:6,7-di-O-isopropylidene-D-glycero-D-talo-heptono-1,5-lactone.

These reactions were carried out as follows, in which compound numbers in parentheses correspond to the compounds shown by structure hereinbefore:

The talo-hydroxylactone (1) was esterified with triflic anhydride to give the stable talo-triflate (2) in 93% yield. Reaction of the triflate (2) with excess sodium azide in dimethyl formamide at room temperature for 4 h gave the talo-azide (5) in 81% yield in which the configuration at C TM 2 of the lactone had been retained. It was found, by monitoring the progress of the azide displacement reaction by TLC, &hat nearly all the triflate (2) first gives the inverted galacto-azide (6) which equilibrates under the reaction conditions to the more stable talo-azide. Thus the galacto-azide (6) may be isolated in 54% yield [based on unrecovered triflate (2) under kinetic conditions; this yield for the preparation of (6) has not yet been optimized.

The isolated galacto-azide (6) is shown herein to equilibrate to the talo-azide (5) both under the reaction conditions for the displacement and also on treatment with sodium acetate in dimethyl formamide. When the triflate (2) was treated with sodium azide in dimethyl formamide in the presence of deuterium oxide and the reaction mixture worked up after 4 min., the starting talo-triflate (2) was recovered in 46% yield with 60% deuterium incorporated at C-2 and the galacto-azide (6)

was isolated in 37% yield with 50% deuterium incorporated at C-2; a small amount (about 2%) of the talo-azide (5) was isolated with 90% deuterium incorporated at C-2. No qalactotriflate (4) was isolated from the reaction mixture. When the azide displacement in the presence of deuterium oxide was run for 90 min, no triflates were isolated but both talo-azide (37% yield) and the galacto-azide (38% yield), each with greater than 90% deuterium incorporation at C-2 were formed.

The galacto-hydroxyactone (3) was also esterifed with triflic anhydride to give the qalactotriflate (4) in high yield; however, in contrast to the kinetic stability of the talo-triflate (2) (4) is more labile and decomposes on standing at room temperature. Nonetheless, (4) undergoes an efficient displacement of triflate by azide with inversion of configuration to give the talo-azide (5) in 82% yield. It was initially assumed that the inverted azide (5) was formed by a direct displacement reaction; however, investigation of the reaction by TLC showed that the triflate (4) was consumed rapidly to give a mixture containing the epimeric triflate (2), the galacto-azide (6) and a minor amount of the talo-azide (5). The galacto-triflate (4) was rapidly epimerized to the talo-triflate by treatment with sodium acetate in dimethyl formamide. Thus the major pathway for the formation of the talo-azide (5) from galacto-triflate (4) involves initial epimerization of (4) to the talo-triflate (2), direct displacement to give the galacto-azide (6), followed by a second epimerization to give the thermodynamically more stable azide (5).

Further evidence for the double epimerization pathway was provided by deuterium incorporation tests. Thus treatment of (4) with sodium azide in dimethyl formamide in the presence of deuterium oxide for 10 min at room temperature gave talo-triflate (33% isolated yield with greater than 90% deuterium incorporated at C-2), galacto-azide (6) (30% isolated yield with greater than 90% deuterium incorporated at C-2), and talo-azide (5) (16%, isolated yield with 20% deuterium incorporated at C-2); no galacto-triflate was recovered from the reaction mixture. These results indicate that the predominant pathway for the formation of the talo-azide involves a double epimerization and that direct displacement of triflate by azide constitutes a minor competing pathway.

Although the coupling constants ($J_{H-2, H-3}$), between the talc,-compounds (1) (3.5 Hz), triflate (2) (3.3 Hz) and azide (5) (3.3 Hz) were consistently higher than those for the galactocompounds (3) (2.5 Hz) and azide (6) (2.1 Hz), such small differences could not reasonably be used with confidence to establish the stereochemistry of the substituent at C-2. The structures of the talohydroxylactone (1) and the talo-azidolactone (5) were firmly established by single crystal x-ray analysis. The high carbonyl stretching frequencies (up to 1793 cm$^{-1}$) of all the 1,5-lactones disclosed herein are consistent with boat conformations for all the compounds reported. [Mirza et al., Helv. Chim. Acta, 68, 988 (1985); Overton et al., J. Chem. Soc. C, 1482 (1965)].

All the results herein also are consistent with the hypothesis that the galacto-compounds (3), (4) and (6) are thermodynamically less stable than the corresponding talo-isomers (1), (2) and (5) because in the boat form of the galacto-isomers the 2-substituent is in a flag-pole position whereas in the talo-compounds the substituents are in less sterically hindered bowsprit positions. Thus the equilibrations of the galacto-triflate and the galacto-azide to the corresponding talo-isomers may take place via the anion derived by removal of the proton at C-2. Also, the direct displacement of triflate from the galactotriflate (4) by azide is slower than equilibration of (4) to the more stable talo-epimer (2); thus the apparent inversion by azide in the displacement of triflate from C-2 of the galactono-lactone (4) occurs by epimerization of (4) to the more stable triflate (2) followed by displacement with inversion to give the less stable azide (6) which subsequently isomerizes to the more stable azide (5).

The triflate of a protected ribono-1,5-lactone (8) has been shown to undergo nucleophilic displacement by azide in high yield to give the ribo-azide (9) in which the configuration at C-2 is retained; (2) has been used for the synthesis of D-amino acids such as (2R, 3S, 4R)-dihydroxyproline (10). [Baird et al, J. Chem. Soc., Perkin Trans 1, 1785–1791 (1987); Dho et al., Tetrahedron Lett. 27, 3203–3204 (1986).] The talo-azide (5), with 5 adjacent chiral centres, is an intermediate which can be used for the synthesis of α-amino acids with seven adjacent functional groups and five adjacent chiral centres, and may also provide strategies for the synthesis of such highly functionalized alkaloids as alexine (11) [Nash et al., Tetrahedron, 44, 5959–5964 (1988)]; and homonojirimycin (12) [Kite et al., Tetrahedron Lett. 29, 6483–6486 (1988)]. The taloazide allows the synthesis of L-amino acids as distinguished from the prior ribo-azide work which produces non-naturally occurring D-amino acids.

Other suitable azide cations for use in the azide displacement reaction of the invention are potassium, tetra-butylammonium, lithium and the like. Other suitable organic solvents for use in this reaction are N-methyl-pyrrolidine, acetone, acetonitrile, dimethylsulfoxide and the like. Suitable protecting groups for the heptonolactone 2-O-trifluoromethanesulfonates used in the azide displacement reaction can be introduced by reaction with ketones and dialkylketones such as for example, acetone, 3-pentanone, dihexylketone, cyclohexanone and the like.

The following examples will further illustrate the invention in greater detail although it will be appreciated that the invention is not limited to these specific examples.

METHODS

M.p.s were recorded on a Kofler block. Infra red spectra were recorded in solution on a Perkin-Elmer 781 spectrophotometer. Optical rotations were measured on a Perkin-Elmer 241 polarimeter; concentrations are given in g/100ml. $^1$H NMR spectra were run at 200 MHz on a Varian Gemini 200 spectrometer, or at 300 MHz on a Bruker WH 300 spectrometer. $^{13}$C NMR spectra were recorded on a Varian Gemini (50 MHz) spectrometer. Mass spectra were recorded on VG Micromass ZAB 1F spectrometer. Microanalyses were performed by the microanalytical services of the Dyson Perrins Laboratory, Oxford, U.K. TLC was performed on glass plates coated with silica gel Blend 41, and compounds %;ere visualized with a spray of 0.2% w/v ceric sulphate and 5% ammonium molybdate in 2M sulphuric acid. Flash chromatography was carried out using Merck Kieselgel 60, 230–400 mesh. Dimethyl formamide and dichloromethane were distilled from calcium hydride immediately prior to use. D-Mannose was obtained from Sigma Chemical Company and was converted into 2,3:5,6-di-O-isopropylidene-D-mannofuranose in 80%–90% yield as previously described by Schmidt, Meth. Carbohydr. Chem. 2, 318 (1963).

EXAMPLE 1

3,4:6,7-Di-O-isopropylidene-D-glycero-D-talo-heptono1,5-lactone (1) and 3,4:6,7-Di-O-isopropylidene-D-glycero-D-galactoheptano-1,5-lactone (3). A mixture 2,3:5,6-di-O-isopropylidene-D-mannofuranose (7) (10.8 g, 41.0 mmol), sodium cyanide (1.84 %% 38.0 mmol) and sodium hydrogen carbonate (3 g) in water (200 ml) was stirred at room temperature for 4 days after which time a clear solution was obtained which was free of cyanide. The reaction mixture was then heated at 90° C. for 1.5 h, cooled to room temperature and extracted with dichloromethane (2×20 ml); the dichloromethane layer was dried (sodium sulphate) and the solvent removed to give unreacted starting material (7) (1.84 g, 17%). The aqueous layer was adjusted to pH 3 by dropwise addition of concentrated sulphuric acid and then extracted with ethyl acetate (3×150 ml). The combined ethyl acetate extracts were dried (sodium sulphate) and the solvent removed to give a residue which, after purification by flash chromatography [ethyl acetate:hexane, 1:2], gave the following two products:

A 3,4:6,7-di-O-isopropylidene-D-glycero-D-qalactoheptono-1,5-lactone (3), $R_f$ 0.7 (ethyl acetate:hexane, 2:1) and $R_f$ 0.6 (ethyl acetate hexane, 1:1), (0.78 g, 6.6% yield, 8% based on unrecovered starting material), m.p. 140°–141° C. (ether:hexane), $[\alpha]_D^{20} +93.4°$ (c, 1.2 in $CHCl_3$), $v_{max}$ ($CHCl_3$): 3350 (OH), 1755 (C=O) $C^{-1}$; (Found: C, 54.17; H, 7.25. $C_{13}H_{20}O_7$ requires: C, 54.16; H, 7.01%), and

B 3,4:6,7-di-O-isopropylidene-D-glycero-D-talo-heptono1,5-lactone (1). $R_f$ 0.5 (ethyl acetate:hexane, 2:1) and $R_f$ 0.3 (ethyl acetate:hexane, 1:1), 3.08 g, 26% yield, 31% based on unrecovered starting material), m.p. 157°–159° C. (ethyl acetate:hexane), $[\alpha]_D^{20} +63.8°$ (c, 1.3 in $CHCl_3$), $v_{max}$ ($CHCl_3$): 3540 (OH), 1767 (C=O) $C^{-1}$; (Found C, 54.12; H, 7.09. $C_{13}H_{20}O_7$ requires: C, 54.16; H, 7.01%).

EXAMPLE 2

3,4:6,7-Di-O-isopropylidene-2-0-trifluoromethanesulphonyl-D-91ycero-D-talo-heptono-1,5-lactone (2). Dry pyridine (4 ml, 50 mmol) and trifluoromethanesulphonic anhydride (5.0 g, 18 mmol) were added over 5 min to a stirred solution of the talo-lactone (1) (3.72 g, 13 mol) in dichloromethane (75 ml) at −30° C. under nitrogen; after a further 5 min, no starting material remained and the reaction was quenched by addition of dilute aqueous hydrochloric acid (60 ml). The organic layer was washed with brine (2×60 ml) and dried (sodium sulphate); the solvent was removed to give the stable crude triflate (2), a cream solid, (5.1 g, 93%), which was used directly for the conversion to azide without further purification. A sample of the crude triflate was recrystallized to give 3,4:6,7-di-O-isopropylidene-2-0-trifluoromethanesulphonyl-D-glycero-D-talo-heptono-1,5-lactone (2). m.p. 118°–119° C. (dec.) (ether:hexane), $[\alpha]_D^{20} +37.0°$ (c, 1.02 in $CHCl_3$), $v_{max}$ ($CHCl_3$): 1793 (C=O) $cm^{-1}$; Found: C, 40.05; H, 4.59. $C_{14}H_{19}F_3O_9S$ requires: C, 40.00; H, 4.56%).

EXAMPLE 3

3,4:6,7-Di-O-isopropylidene-2-0-trifluoromethanesulphonyl-D-glycero-D-galacto-heptono-1,5-lactone (4). Dry pyridine (0.5 ml, 6 mmol) and trifluoromethanesulphonic anhydride (670 mg, 2.4 mmol) were added to a stirred solution of galacto-lactone (3) (465 mg, 1.6 mmol) in dichloromethane (20 ml) at −30° C. under nitrogen; after stirring for a further 2 h at −20° C., only a little starting material remained and the reaction was quenched by addition of dilute aqueous hydrochloric acid (10 ml). The organic layer was washed with brine (10 ml) and dried (sodium sulphate); the solvent was removed and the residue purified by flash chromatography [ethyl acetate:hexane, 1.4] to give 3,4:6,7-di-O-isopropylidene-2-O-trifluoromethanesulphonyl-D-glycero-D-galacto-heptono-1,5-lactone (4), (564 mg, 84%), (Found: C, 39.5; H, 4.9. $C_{14}H_{19}F_3O_9S$ requires: C, 40.00; H, 4.56%). In contrast to the talotriflate (2), this galacto-triflate (4) decomposed and darkened at room temperature rapidly and had to be used immediately in the next step [see Example 5(ii), below]; it was advantageous to purify this triflate by flash chromatography to obtain good yields in the subsequent displacement step.

EXAMPLE 4

2-Azido-2-deoxy-3,4:6,7-di-O-isopropylidene-D-glycero-D-talo-heptono-1,5-lactone (5).

(i) From talotriflate (2). The crude triflate (2) (5.1 g, 12 mmol), prepared above in Example 2, in dimethyl formamide (25 ml) was stirred with sodium azide (1.0 g, 15 mmol) at room temperature for 4 h. The solvent was then removed and the residue partitioned between dichloromethane (60 ml) and brine (60 ml). The organic layer was dried (sodium sulphate) and the solvent removed to give, after purification by flash chromatography [ethyl acetate:hexane, 1:3], 2-azido-2-deoxy-3,4:6,7-di-O-isopropylidene-D-glycero-D-talo-heptono-1,5-lactone (5). [3.05 g, 81%, 75% from alcohol (1)], as a colorless syrup which crystallized on standing m.p. 103°–104° C. (ether:hexane), $[\alpha]_D^{20} +96.7°$ (c, 1.13 in $CHCl_3$), $v_{max}$ ($CHCl_3$): 2125 ($N_3$), 1773 (C=O) $C^{-1}$; Found: C, 49.81; H, 6.19; N, 13.70. $C_{13}H_{19}N_3O_6$ requires: C, 49.84; H, 6.11; N, 13.41%).

(ii) From galacto-triflate (4). The purified galacto-triflate (4) (472 mg, 1.1 mmol), prepared above in Example 3, in dimethyl formamide (5 ml) was stirred with sodium azide (292 mg, 4.5 mmol) at room temperature for 4 h. The solvent was then removed and the residue was extracted with dichloromethane (30 ml); the organic extract was then washed with brine (3×20 ml), dried (sodium sulphate) and the solvent removed. The residue was purified by flash chromatography [ethyl acetate:hexane, 1:3 to give the talo-azide (5), (288 mg, 82%), identical in all respects to the material made in (i) above.

EXAMPLE 5

2-Azido-2-deoxy-3,4:6,7-di-isopropylidene-D-glycero-D-galacto-heptono-1,5-lactone (6).

(i) From talo-triflate (2). The crude triflate (2) (200 mg, 0.48 mmol) in dimethyl formamide (5 ml) was stirred with sodium azide (20 mg, 0.30 mmol) at room temperature for 3 h. The solvent was then removed and the residue partitioned between dichloromethane (20 ml) and brine (30 ml). The organic layer was dried (sodium sulphate) and the solvent removed to give after purification by flash chromatography [ethyl acetate: hexane, 1:4] three compounds. The first compound eluted was 2-azido-2-deoxy-3,4:6,7-di-O-isopropylidene-D-glycero-D-galacto-heptono-1,5-lactone (6). (60 mg, 40%, 54% based on unrecovered starting material), m.p. 89° ∝ 90° C. (ether:hexane), $[\alpha]_D^{20}$ +164.1° (c, 1.05 in CHCl₃), $\nu_{Max}$ (CHCl₃): 2120 (N₃) 1760 (C=O) C⁻¹; (Found: C, 49.55; H, 6.26; N, 13.47. $C_{13}H_{19}N_3O_6$ requires: C, 49.84; H, 6.11; N, 13.14%). The second compound to be eluted was unreacted talotriflate (2), (52 mg, 26%), while the third compound was the talo-azide (5), 3 mg, 2%).

(ii) From galacto-triflate (4). The galacto-triflate (4), prepared as described above, in Example 3, immediately prior to use, from the galacto-lactone (3), 2.9 g, 10 mmol), was stirred with sodium azide (2.3 g, 35 mmol) in dimethylformamide (7 ml) at room temperature for 2 h, after which time dichloromethane (20 mL) was added. The reaction mixture was filtered and the solvent removed; the residue was purified by flash chromatography [ethyl acetate:hexane, 1:3]to give the galacto-azide (6), 1.10 q, 35% from galacto-lactone (3), and the talo-azide (5), 0.91 g. 29% from galacto-lactone (3)]. TLC [ethyl acetate:hexane, 1:2] of the reaction mixture indicated that the galacto-triflate (4) ($R_f$ 0.7) was consumed within a few minutes of the reaction, while the intermediate talo-triflate (2) ($R_f$ 0.6) was consumed in 2 h to give circa 1:1 mixture of galacto-azide (6) ($R_f$ 0.65) and talo-azide (5) ($R_f$ 0.45).

EXAMPLE 6

Conversion of galacto-azide (6) to the talo-azide (5). The galacto-azide (6) (68 mg, 0.22 mmol) in dimethyl formamide (1 ml) was stirred with anhydrous sodium acetate (53 mg, 0.65 mmol) at room temperature for 3 h. After addition of dichloromethane (10 ml) and filtration, the solvent was removed to give a residue which on purification by flash chromatography [ethyl acetate:hexane, 1:5] gave the talo-azide (6) (46 mg, 68%) and galacto-azide (6) (8 mg, 11%). A similar conversion was observed when sodium azide was used instead of sodium acetate.

EXAMPLE 7

Conversion of galacto-triflate (4) to the talotriflate (2). Anhydrous sodium acetate (45 mg, 0.55 mmol) was added in one portion to a stirred solution of purified galacto-triflate (4) (77 mg, 0.18 mmol) in dimethyl formamide (1 ml). TLC (ethyl acetate:hexane, 1:2) after 2 min indicated that starting material (4) ($R_f$ 0.7) had been completely converted to the talo-triflate (2) ($R_f$ 0.6). The reaction mixture was diluted with dichloromethane (5 ml), filtered and the solvents removed to give, after flash chromatography [ethyl acetate:hexane, 1:4], the talo-triflate (2) (59 mg, 77%).

General procedure for deuterium exchange tests. The triflate or azide (0.2 to 0.7 mmol) was stirred [with a relevant amount of sodium azide in dimethyl formamide (1 to 2 ml) containing 5–10% v/v deuterium oxide at room temperature. After an appropriate time interval (several minutes), dichloromethane (10 ml) was added, and the reaction mixture filtered and the solvent removed to give a residue which was purified by flash chromatography. The amount of deuterium incorporated at C-2 by the procedure was determined from the relative reduction in intensity of the H-2 doublet in the 200 MHz ¹H NMR spectra.

X-Ray Crystal Structure Analyses. The structures of 3,4:6,7-di-O-isopropylidene-D-glycero-D-talo-heptono-1,5-lactone (1) (crystallized from ethyl acetate:hexane) and of 2-azido-2-deoxy-3,4:6,7-di-O-isopropylidene-D-glycero-D-talo-heptono-1,5-lactone (5) (crystallized from ether:hexane) were established by single crystal x-ray analyses.

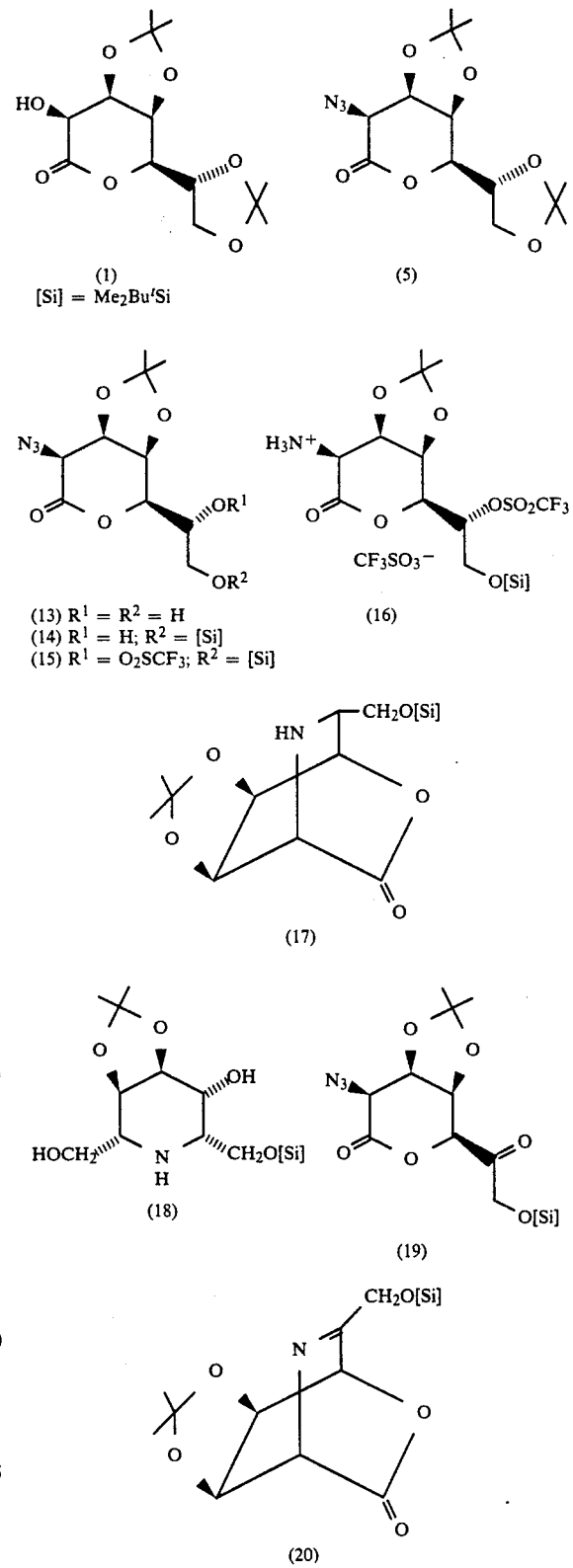

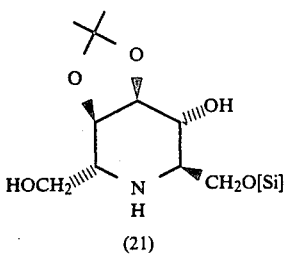

(21)

EXAMPLE 8

2-Azido-2-deoxy-3,4-0-isopropylidene-D-glycero-D-talo-heptono-1,5-lactone (13). 2-Azido-2-deoxy-3,4:6,7-di-O-isopropylidene-D-glycero-D-talo-heptono-1,5-lactone (5) (815 mg, 2.6 mmol) was stirred with 80% acetic acid (6 ml) for 3.5 h at 50° C. The solvent was removed and the residue was purified by flash chromatography [ethyl acetate:hexane, 4:1] to give 2-azido-2-deoxy TM 3,4-O-isopropylidene-D-glycero-D-talo-heptono-1,5lactone (13), (672 mg, 94%), m.p. 126°-127° C. (ethyl acetate-hexane), $[\alpha]_D^{20} + 131.5°$ (c, 1.08 in MeOH). $\nu_{max}$ (nujol): 3470 (OH), 2120 (N$_3$), 1750 (C=O) C$^{-1}$. (Found C, 44.02; H, 5.47; N, 15.22 C$_{10}$H$_{15}$N$_3$O$_6$ requires: C, 43.96; H, 5.53; N, 15.38%)

EXAMPLE 9

2-Azido-7-0-tert-butyldimethylsilyl-2-deoxy-3,4-O-isopropylidene-D-glycero-D-talo-heptono-1,5lactone (14). A solution of tert-butyldimethylsilyl chloride (0.95 g, 6.3 mmol) in dimethylformamide (5 ml) was added dropwise, under nitrogen, to a stirred solution of the diol (13) (1.15 g, 4.2 mmol) and imidazole (0.57 g, 8.4 mmol) in dimethylformamide (15 ml) at $-10°$ C. After 15 min at $-10°$ C. the reaction was complete and the solvent was removed. Purification by flash chromatography [hexane:ethyl acetate, 4:1] gave 2-azido-7-O-tert-butyldimethylsilyl-2-deoxy-3,4-O-isopropylidene-D-glycero-D-talo-heptono-1,5-lactone (14). (1.29 g. 79%) a white solid, m.p. 138° -139° C. (ether), $[\alpha]_D^{20} + 109.6°$ (c, 0.99 in CHCl$_3$). $\nu_{max}$ (CHCl$_3$): 3550 (OH), 2120 (N$_2$), 1779 (C=O) C$^{-1}$. (Found C, 49 34; H, 7.77; N, 10.59. C$_{16}$H$_{29}$N$_3$O$_6$Si requires: C, 49.59; H, 7.54; N, 10.84%).

EXAMPLE 10

2-Azido-7-0-tert-butyldimethylsilyl-2-deoxy-3,4-O-isopropylidene-6-O-trifluoromethanesulphonyl-D-glycero-D-talo-heptono-1,5-lactone (15). Dry pyridine (0.8 ml, 10 mmol) and trifluoromethanesulphonic anhydride (1.22 g, 4.3 mmol) were added to a stirred solution of 2-azido-2-deoxy-3,4–0-isopropylidene-7-0-tert-butyl-dimethylsilyl-D-glycero-D-talo-heptono-1,5-lactone (14) (1.29 g, 3.3 mmol) in dichloromethane (15 ml), under nitrogen, at $-20°$ C. After 30 min at $-10°$ C., tlc [ether:hexane, 1:1] indicated complete consumption of starting material ($R_f$ 0.2) to give a single product ($R_f$ 0.6). The reaction was diluted with dichloromethane (20 ml), washed with dilute aqueous hydrochloric acid (2×10 ml), followed by brine (20 ml), and dried (sodium sulphate). The solvent was removed to give the triflate (1.62 g, 95%), a yellow crystalline solid which was used without purification. A small sample was recrystallized to give colorless needles of 2-azido-7-O-tert-butyldimethylsilyl-2-deoxy-3,4-O-isopropylidene-6-O-trifluoromethanesulphonyl-D-glycero-D-talo-heptono-1,5-lactone (15). m.p. 79°-80° C. $[\alpha]_D^{20} + 41.1°$ (c, 0.95 in CHCl$_3$), $\nu_{max}$ (CHCl$_3$): 2125 (N$_3$), 1780 (C=O) cm$^{-1}$. (Found C, 39.45; H, 5.43; N, 8.26. C$_{17}$H$_{28}$F$_3$N$_3$O$_8$SS$_1$ requires C, 39.30; H, 4.53; N, 8.09%).

EXAMPLE 11

2-Amino-7-0-tert-butyldimethylsilyl-2-deoxy-3,4-O-isopropylidene-6-O-trifluoromethanesulphonyl-D-glycero-D-talo-heptono-1,5-lactone trifluoromethane-sulphonate (16). A solution of the triflate (15) (1.62 g, 3.12 mmol) in ethyl acetate (20 ml) was stirred vigorously at room temperature, under hydrogen, in the presence of 10% palladium on carbon (100 mg). After 24 h no starting material remained by tlc ($R_f$ 0.6, ether:-hexane, 1:1). The mixture was filtered through celite, washing with ethyl acetate (30 ml), to give a solution containing two products ($R_f$, 0.95 and 0.4, ethyl acetate) The solvent was removed and the residue was purified by flash chromatography (ethyl acetate:hexane, 2:1) to give two compounds; the first was the bicyclic amine (15) (550 mg, 52%), identical in all respects to the material prepared below. The second compound was identified as the triflate salt, 2-Amino-7-0-tert-butyldimethylsilyl-2-deoxy-3,4-O-isopropylidene-6-O-trifiluoromethanesulihonyl-D-glycero-D-talo-heptono-1,5-lactone trifluoromethanesulphonate (16) (872 mg, 43%), a white solid, m.p. 77°-79° C. (ether), $[\alpha]_D^{20} + 34.7°$ (c, 1.0 in CHCl$_3$), $\nu_{max}$ (CHCl$_3$): 3500 br (NH$_3$+), 1780 (C=O) C$^{-1}$. (Found: C, 33.46; H, 5.04; N, 2.13. C$_{18}$H$_{31}$F$_6$NO$_{11}$S$_2$Si requires: C, 33.59; H. 4.85; N, 2.18%).

EXAMPLE 12

7-O-tert-Butyldimethylsilyl-2,6-dideoxy-2,6-imino-3,4-O-isopropylidene-L-glycero-D-talo-heptono-1,5-lactone (17). The azido triflate (15) (605 mg, 1.16 mmol) in ethyl acetate (20 ml) was stirred vigorously at room temperature, under hydrogen, in the presence of anhydrous sodium acetate (380 mg, 4.6 mmol) and 10% palladium on carbon (50 mg). After 20 h. the mixture was filtered through celite, washed with ethyl ace%ate (20 ml), to give a colorless solution showing one spot on tlc [ethyl acetate, $R_f$ 0.9]. Flash chromatography (hexane:ethyl acetate, 1:1) gave 7-0-tert-butyldimethylsilyl-2,6-dideoxy-2,6-imino3,4-O-isopropylidene-L-glycero-D-talo-heptono-1,5-lactone (17) (348 mg, 96%, a colorless syrup which solidified to a white wax on standing. $[\alpha]_D^{20} - 15.4°$ (c 1.2 in CHCl$_3$). $\nu_{max}$ (neat): 3360 (NH), 1781 (C=O) cm$^{-1}$; (Found: C, 55.17; H, 8.79: N, 4.27. C$_{16}$H$_{29}$NO$_5$Si requires: C, 55.95: H, 8.51; N, 4.08%).

EXAMPLE 13

Cyclization of the triflate salt (16) to the bicyclic amine (17)

Method (i). The triflate salt (16) (105 mg, 0.16 mmol) was stirred wi%h anhydrous sodium acetate (54 mg, 0.65 mmol) in dimethyl formamide (4 m) at room temperature for 20 h. The solvent was removed and the residue was purified by flash chromatography (hexane: ethyl acetate, 2.1) to give the bicyclic amine (17) (47 m%, 86%), identical in all respects to the material prepared above.

Method (ii). The triflate salt (16) (75 mg, 0.12 mmol) was stirred with anhydrous sodium carbonate (25 mg, 0.24 mg) in dry tetrahydrofuran (3 ml). After 24 h at room temperature the reaction was worked up and purified as above to give the bicyclic amine (17) (30 mg, 79%).

EXAMPLE 14

7-O-tert-Butyldimethylsilyl-2,6-dideoxy-2,6-imino3,4-O-isopropylidene-L-glycero-D-talo-heptitol (18), Method (i). Lithium aluminum hydride (50 mg, 1 mmol) was added to a stirred solution of the bicyclic amine (17) (167 mg, 0.48 mmol) in dry THF (3 ml) at 0° C. After 2 h at 0° C. tlc (hexane:ethyl acetate, 2:1) indicated complete consumption of starting material ($R_f$ 0.6) to give a product at $R_f$ 0.1 together with baseline material. The reaction was quenched with water (0.5 ml), diluted with ethyl acetate (10 ml) and filtered through celite. The solvent was removed and the residue was purified by flash chromatography (hexane:ethyl acetate, 3:2) to give 7-O-tert-butyl dimethylsilyl-2,6-dideoxy-2,6-imino-3,4-O-isopropylidene-L-glycero-D-talo-heptitol (18) (90 mg, 54%), m.p. 112°–114° C. (ether-hexane), $[\alpha]_D^{20}$ +52.7° (c, 1.0 in CHCl$_3$, $\nu_{max}$(CHCl$_3$): 3450 (NH cm$^{-1}$. (Found: C, 55.46; H, 9.51; N, 4.03. C$_{16}$H$_{35}$NO$_5$Si requires: C, 55.30; H, 9.57; N, 4.03%).

Method (ii). Lithium borohydride (2 M in THF, 0.55 ml, 1.1 mmol) was added to a stirred solution of the bicyclic amine (17) (379 mg, 1.1 mmol) in THF (10 ml), under nitrogen, at —20° C. The solution was allowed to warm to room temperature and stirred for 2 h, after which time tlc (hexane:ethylacetate 1:1) indicated only a trace of starting material ($R_f$ 0.7) and two products at $R_f$ 0.6 and 0.1. The reaction was quenched with anhydrous ammonium chloride, filtered, and the solvent removed to give a solid (383 mg) Flash chromatography (hexane:ether, 2:1) gave two products; the first was the borane adduct (153 mg, 39%), m.p. 110° C. (dec., ether-hexane), $[\alpha]_D^{20}$ +9.8° (c 1.0 in CHCl$_3$), $\nu_{max}$ (CHCl$_3$): 3450, 3230 (NH and OH), 2380 (BH$_3$) C$^{-1}$. (Found: C, 53.81; H, 10.34; N, 3.60. BC$_{16}$H$_{32}$NO$_5$Si requires: C, 53.18; H, 10.04; N, 3.88%). The second product was identified as 7-O-tert-butyldimethylsilyl-2,6-dideoxy-2,6-imino3,4-O-isopropylidene-L-glycero-D-talo-heptitol (18) (74 mg, 18%), identical in all respects to the material prepared above.

EXAMPLE 15

2,6-Dideoxy-2,6-imino-L-glycero-D-talo-heptitol hydrochloride (6-epi-HMJ). 7-O-tert-Butyldimethylsilyl-2,6-dideoxy-2,6-imino-3,4-O-isopropylidene-L-glycero-D-talo-heptitol (18) (137 mg, 0.40 mmol) was stirred in 50% aqueous trifluoroacetic acid (4 ml) for 20 h at room temperature. The solvent was removed an the crude trifluoroacetate salt was decomposed with dilute aqueous sodium hydroxide. Purification by ion exchange chromagoraphy (Dowex 50 x, 8-100, H+ form, eluting with 0.5 M aqueous ammonia), followed by freeze drying, gave 2,6-dideoxy-2,6-imino-L-glycero-D-talo-heptitol (6-epi-HMJ), (66 mg, 85%), a very hygroscopic solid, ($R_f$ 0.8, EtOH:MeOH:0.5 M NH$_3$ 2:2:1), $[\alpha]_D^{20}$+26.4° (c, 0.5 in H$_2$O). Repeating this procedure with the borane adduct (125 mg, 0.35 mmol) gave an identical material to that above (55 mg, 82%). The free base (18) (100 mg, 0.52 mmol) was dissolved in methanol (3 ml) and acetyl chloride (ca. 0.1 ml, 1 mmol) was added. Addition of chloroform and cooling yielded crystals of 2,6-dideoxy-2,6-imino-L-glycero-D-talo-heptitol hydrochloride, (91 mg, 76%), m.p. 203°–205° C. (methanol:chloroform), $[\alpha]_D^{20}$+31.1° (c, 1.0 in H$_2$O), $\nu_{max}$(KBr): 3500-2500 (NH, OH) cm$^{-1}$. Found: C, 36.61; H, 7.32; N, 5.88. C$_7$H$_{16}$NO$_5$Cl requires: C, 36.61; H, 7.02; N, 6.10%.

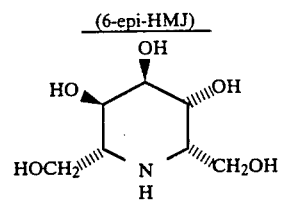

EXAMPLE 16

2-Azido-7-O-tert-butyldimethylsilyl-2-deoxy-3,4-O-isopropylidene-D-talo-6-heptulosono-1,5-lactone (19). The alcohol (14) (2.07 g, 5.35 mmol) and pyridinium chlorochromate (3.45 g, 16 mmol) were stirred with powdered molecular sieve (2 g) in dichloromethane (50 ml), under nitrogen, at room temperature. After 18 h, tlc (hexane:ethyl acetate, 1:1) indicated complete consumption of starting material ($R_f$ 0.35) to give a single product ($R_f$ 0.5). The mixture was diluted with ether (50 ml), filtered through a celite plug and the solvent removed. Flash chromatography (hexane:ethyl acetate, 5:1) gave 2-Azido-7-O-tert-butyldimethylsilyl-2-deoxy-3,4-O-isopropylidene-D-talo-6-heptulosono1,5-lactone (19), (1.53 g, 7%%), m.p. 120°–122° (ether), $[\alpha]_D^{20}$+5.4° (c, 1.0 in CHCl$_3$), $\nu_{max}$(CHCl$_3$): 2123 (N$_3$), 1780 (C=O), 1743 (C=O) C$^{-1}$. (Found: C, 49.96; H, 7.32; N, 10.60. C$_{16}$H$_{27}$N$_3$O$_6$Si requires: C, 49.85; H, 7.06; N, 10.90%).

EXAMPLE 17

Imine (20)

Triethyl phosphite (1.3 M in THF, 2.4 ml, 3.1 mmol) was added, under nitrogen, to a stirred solution of the ketone (19) (605 mg, 1.57 mmol) in dry THF (5 ml). After 18 h at room temperature, tlc (hexane:ethyl acetate, 5:1) indicated complete consumption of starting material ($R_f$ 0.6) to give a single product ($R_f$ 0.7). The solvent was removed and the residue was purified by flash chromatography (hexane:ethyl acetate, 5:1) to give the bicyclic imine (20), (477 mg, 89%), a colorless oil $[\alpha]_D^{20}$ 98.3° (%, 1.0 in CHCl$_3$), $\nu_{max}$ (film): 1780 (C=O), 1650 (C=N) cm$^{-1}$. (Found: C, 56.39; H, 8.02; N, 4.05. C$_{16}$H$_{27}$NO$_5$Si requires: C, 56.28; H, 7.97; N, 4.10%).

EXAMPLE 18

7-O-tert-Butyldimethylsilyl-2,6-dideoxy-2,6-imino3,4-O-isopropylidene-D-glycero-D-talo-heptitol (21). Lithium borohydride (2 M in THF, 0.6 ml, 1.2 mmol) was added, under nitrogen, to a stirred solution of the imine (18) (182 mg, 0.53 mmol) in dry THF (10 ml) at —78° C. The solution was allowed to warm to room temperature over a period of 1 h and stirred for an additional 4 h before quenching with saturated aqueous ammonium chloride (0.3 ml). The solution was evaporated to dryness and the residue was purified by flash chromatography (gradient elution; hexane:ethyl acetate, 1:1 0:1) to give two products; the first ($R_f$ 0.3, ethyl acetate) was 7-O-tert-butyldimethylsilyl-2,6-dideoxy-2,6-imino-3,4-O-isopropylidene-D-glycero-L-talo-heptitol (18) (3 mg 2%), identical in all respects to the material prepared above. The second compound was identified as 7-O-tert-butyldimethylsilyl-2,6-dideoxy-2,6-imino-3,4-O-isopropyl-idene-D-qlycero-D-talo-heptitol (21), (85 mg, 46%), m.p. 165°–166° C. (ethyl acetate:ether), $[\alpha]_D^{20}$ −28.5° (c, 1.0 in CHCl$_3$), $\nu_{max}$(CHCl$_3$): 3450 (OH) cm$^{-1}$. Found: C, 55.56; H, 10.01; N, 3.99. C$_{16}$H$_{35}$NO$_5$Si requires: C, 55.30; H, 9.57; N, 4.03%).

EXAMPLE 19

2,6-Dideoxy-2,6-imino-D-glycero-D-talo-heptitol (α-HMJ). The protected iminoheptitol (21) (196 mg, 0.56 mmol) in 50% aqueous trifluoroacetic acid (4 ml) was stirred at room temperature for 20 h. After removing the solvent, the resulting trifluoroacetate salt was decomposed to the free base with dilute aqueous sodium hydroxide. Purification by ion exchange chromatography (Dowex 50 x, 8-100, H+ form, eluting with 0.5 M aqueous ammonia solution and then Amberlite CG-400, OH$^1$ form, eluting with water) gave, after freeze drying, 2,6-dideoxy-2,6-imino-D-glycero-D-talo-heptitol (α-HMJ) (99 mg, 92%), a very hygroscopic solid, $[\alpha]_D^{20}$+7.45° (c, 0.55 in H$_2$O).

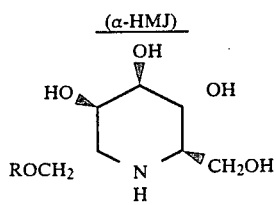

(α-HMJ)

(α-HMJ)

R = H

Various other examples will be apparent to the person skilled in the art after reading the present disclosure without departing from the spirit and scope of the invention. It is intended that all such other examples be included within the scope of the appended claims.

What is claimed is:

1. 2-Azido-2-deoxy-3,4:6,7-di-O-isopropylidene-D-glycero-D-talo-heptono-1,5-lactone.

2. A method for the production of 2-azido-2-deoxy-3,4:6,7-di-O-isopropylidene-D-glycero-D-talo-heptono-1,5-lactone comprising reacting the 2-O-trifluoromethanesulfonate of 3,4:6,7-di-O-isopropylidene-D-glycero-D-taloheptono-1,5-lactone with excess alkali metal azide ion at normal room temperature of about 20–25°C. in organic solvent medium without epimerication at C-2.

3. A method for the production of 2-azido-2-deoxy-3,4:6,7-di-O-isopropylidene-D-glycero-D-talo-heptono-1,5-lactone comprising reacting the 2-O-trifluoromethanesulfonate of 3,4:6,7di-O-isopropylidene-D-glycero-D-galacto-heptono-1,5-lactone with excess alkali metal azide ion at normal room temperature of about 20–25°C. in organic solvent medium accompanied by epimerization at C-2.

* * * * *

UNITED STATES PATENT AND TRADEMARK OFFICE
CERTIFICATE OF CORRECTION

PATENT NO. : 5,021,562

DATED : June 4, 1991

INVENTOR(S) : George W. J. Fleet and Ian Bruce

It is certified that error appears in the above-identified patent and that said Letters Patent is hereby corrected as shown below:

Abstract, line 3, "heltono" should read --heptono--. Col. 2, line 21, "3,4,6,7-di-isopropylidene--"should read --3,4,6,7-di-isopropylidene-D --. Col. 3, line 2, "galacto" should read --talo--. Col. 3, line 46, "13" should read --613--. Col. 4, line 53, "Zhat" should read --that--. Col. 5 line 47, "talc," should read --talo--. Col. 6, line 61, "%;ere" should read --were--. Col. 7, line 9, "%%" should read --g,--. Col. 7, line 27, "D-qalac-" should read --D-galac- --. Col. 7, line 33, "C-1" should read --cm$^{-1}$--. Col. 7, line 44, "C-1" should read --cm$^{-1}$--. Col. 7, line 49 "D-9lycero" should read --D-glycero--. Col. 8, line 44, "C-1" should read --cm$^{-1}$--. Col. 9, line 6, "89°$\times$ 90°C." should read --89°-90°C.-- Col. 9, line 7, "C-" should read --cm$^{-1}$--. Col. 11, line 22, "TM" should be cancelled. Col. 11, line 25, "C-1" should read --cm$^{-1}$--. Col. 11, line 44, "C-1" should read --cm$^{-1}$--. Col. 12, line 30, "C-1" should read --cm$^{-1}$--. Col. 12, line 21, "ace&ate" should read --acetate--. Col. 12, line 57, "wiZh" should read --with--. Col. 13, line 37, "C-" should read --cm$^{-1}$--. Col. 14, line 28, "7%%" should read --74%--. Col. 14, line 30, "C-1" should read --cm$^{-1}$--. Col. 14, line 45, "%" should read --c--.

Signed and Sealed this

First Day of June, 1993

*Attest:*

MICHAEL K. KIRK

*Attesting Officer*  Acting Commissioner of Patents and Trademarks